US007616795B2

(12) United States Patent
Lutz et al.

(10) Patent No.: US 7,616,795 B2
(45) Date of Patent: Nov. 10, 2009

(54) METHOD FOR GENERATING INTERMEDIATE IMAGES WHEN IMAGING WITH THE AID OF A TOMOGRAPHIC IMAGING FACILITY

(75) Inventors: Andreas Lutz, Poxdorf (DE); Werner Schneider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 509 days.

(21) Appl. No.: 11/186,943

(22) Filed: Jul. 22, 2005

(65) Prior Publication Data

US 2006/0036150 A1 Feb. 16, 2006

(30) Foreign Application Priority Data

Jul. 23, 2004 (DE) .................. 10 2004 035 740

(51) Int. Cl.
*G06K 9/00* (2006.01)
*G06K 9/32* (2006.01)

(52) U.S. Cl. .................. 382/128; 382/131; 382/154; 382/300

(58) Field of Classification Search ......... 382/128–134, 382/154, 300; 600/407
See application file for complete search history.

(56) References Cited

U.S. PATENT DOCUMENTS

2005/0041842 A1 * 2/2005 Frakes et al. ................. 382/128

FOREIGN PATENT DOCUMENTS

WO WO 98/36690 * 2/1998
WO WO 98/36690 * 8/1998

OTHER PUBLICATIONS

Office Action for corresponding German Application No. 10 2004 035 740.4-35 dated Apr. 15, 2005.
Office Action for corresponding German Application No. 10 2004 035 740.4-35 dated Jun. 1, 2006.

* cited by examiner

*Primary Examiner*—John B Strege
(74) *Attorney, Agent, or Firm*—Harness, Dickey & Pierce, P.L.C.

(57) ABSTRACT

A method is disclosed for, such as with the aid of a tomographic imaging facility or in particular a computer tomograph, in a number of consecutive measurement scans, acquiring an object volume of an examination object. A series of main images is obtained by reconstructing in each case one main image from measured data of each measurement scan and the main images are displayed in temporal sequence. Intermediate images are calculated in order to raise an image repetition rate and are displayed between the main images. The intermediate images are reconstructed at a prescribable instant within the measurement scan directly from a combination of the measured data, acquired up to this instant, of the respectively current measurement scan with the measured data of the respectively preceding measurement scan. The present method can be used to reduce the delay times in the display of the main images in conjunction with increased image quality of the intermediate images.

8 Claims, 3 Drawing Sheets

FIG 2  Stand der Technik
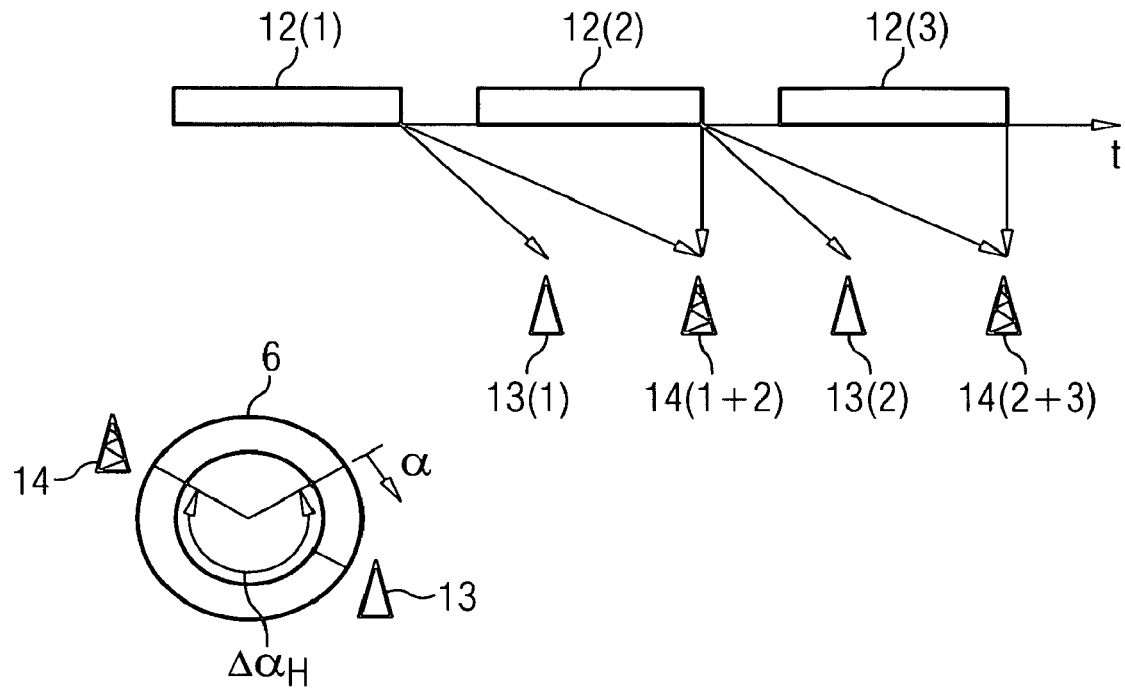
FIG 3
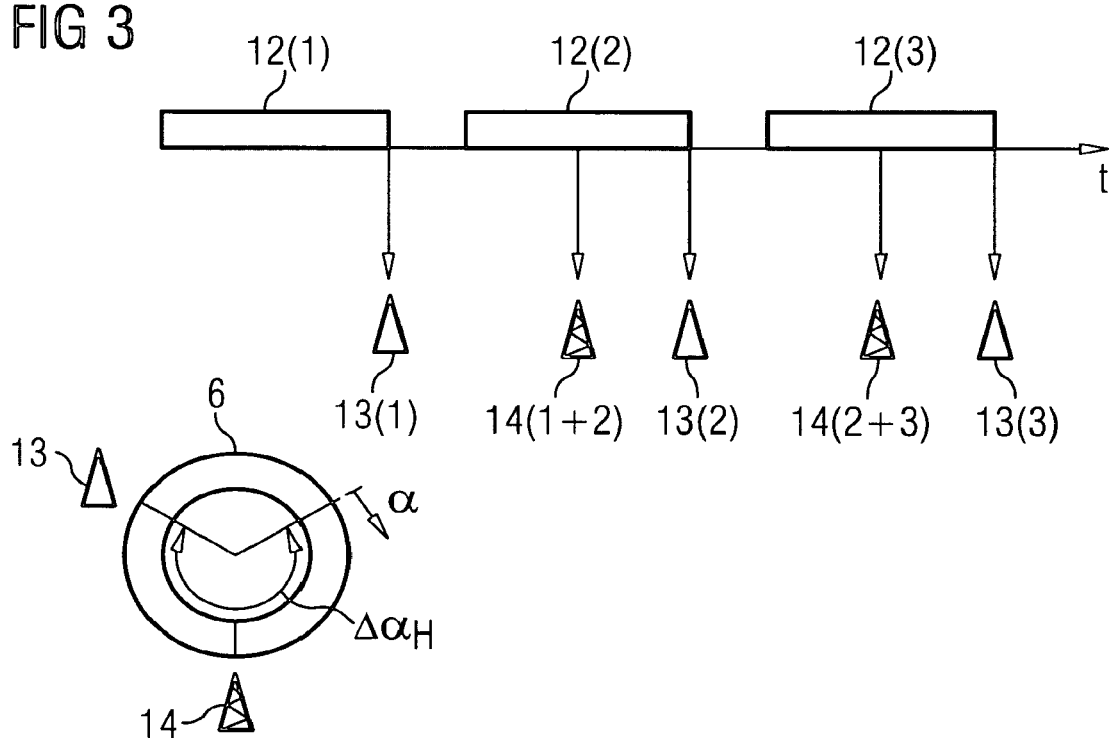

METHOD FOR GENERATING INTERMEDIATE IMAGES WHEN IMAGING WITH THE AID OF A TOMOGRAPHIC IMAGING FACILITY

The present application hereby claims priority under 35 U.S.C. §119 on German patent application number DE 10 2004 035 740.4 filed Jul. 23, 2004, the entire contents of which is hereby incorporated herein by reference.

FIELD

The present invention generally relates to a method for imaging with the aid of a tomographic imaging facility, in particular a computer tomograph. Preferably, in the case of such a method, in a number of consecutive measurement scans, an object volume of an examination object is acquired, a series of main images is obtained by reconstructing in each case one main image from measured data of each measurement scan and the main images are displayed in temporal sequence, intermediate images being calculated in order to raise an image repetition rate and displayed between the main images.

BACKGROUND

When imaging with the aid of tomographic imaging facilities, slice or volume images of the interior of an examination object are obtained. Examples of such tomographic imaging facilities are units for X-ray imaging, in particular computer tomographs and C-arc units, magnetic resonance tomographs, positron emission tomography (PET) units, SPECT (Single Photon Emission Computed Tomography) units or ultrasound tomography units.

Particularly, in the case of invasive medical operations, for his orientation the physician needs online image monitoring of the instruments introduced into the body such as, for example, catheters or biopsy needles. In this case, the tomography images must be displayed in good time, as far as possible. A short latency or delay time on the path between measured data acquisition and image display is therefore of particular importance in these applications.

Invasive operations are monitored by way of X-ray imaging in many instances. In order to reduce the radiation burden on the examining physician during the use of computer tomographs, it is known to switch off the radiation for a specific angular range during each revolution of the rotary frame (gantry) of the computer tomograph. A series of individual measurement scans result in this way.

A main image is reconstructed every complete revolution of the rotary frame from each of these measurement scans with the aid of a suitable algorithm, and subsequently displayed. However, this procedure lowers the image repetition rate considerably by comparison with a continuous measurement mode of the computer tomograph. In order to double this image repetition rate, up to now there has been inserted in each case between two temporally consecutive main images a synthetic intermediate image that is interpolated from the image data of these main images.

However, in this technique an intermediate image relating to two consecutive measurement scans n−1 and n can be calculated at the earliest when the current measurement scan n is terminated. The shortest possible latency time for displaying the main images is reached when the generation of the intermediate image is positioned at the end of the current measurement scan n. In order for all the images to appear at an interval of half a rotation of the rotary frame, however, in this case the display of the main image that is reconstructed from this measurement scan and is qualitatively of a substantially higher value must be artificially delayed by the time of half a rotation of the rotary frame.

Furthermore, the generation of the intermediate images by interpolation of the pixel intensity between two main images supplies adequate results only for scenes in which the image brightness of a location-varies over time such as, for example, in the case of bolus injections. However, when displaying images of scenes in which the location of an object changes over time, for example during biopsy, this type of interpolation supplies only a superposition of the initial and final positions of the object and not, as aimed at, the intermediate position.

WO 98/36690 A1 discloses a method for dynamic real-time image reconstruction in the case of which a starting image is firstly reconstructed from measured data of a complete measurement scan and is subsequently updated with additional measured data that originate from a subsequent partial scan at the respective slice position. The updating of the starting image is performed by adding an image matrix to the image just displayed. The added image matrix is obtained from a combination of the measured data additionally acquired by the partial scan with the measured data of the original measured scan, which correspond to the same scanning section.

SUMMARY

An object of at least one embodiment of the present invention resides in specifying a method for generating intermediate images with the aid of a tomographic imaging facility. With the aid of a method in at least one embodiment, it is possible to achieve a shorter latency time of the main images and an enhanced image quality of the intermediate images.

In the case of a method of at least one embodiment for imaging with the aid of a tomographic imaging facility, in particular a computer tomograph, in a number of consecutive measurement scans, an object volume of an examination object is acquired, a series of main images is obtained by reconstructing in each case one main image from measured data of each measurement scan and the main images are displayed in temporal sequence. In order to raise an image repetition rate, intermediate images are calculated and displayed between the main images. The method of at least one embodiment is distinguished in that the intermediate images are reconstructed at a prescribable instant within the measurement scan directly from a combination of the measured data, acquired up to this instant, of the respectively current measurement scan with the measured data of the respectively preceding measurement scan.

In the case of a method of at least one embodiment, the intermediate images are therefore reconstructed at any desired prescribable instant within the measurement scans directly from the measured data, that is to say from the raw data of the detectors, if appropriate after a conventional conditioning. The measured data still missing for the current measurement scan that relate to such a reconstruction are taken from the preceding measurement scan.

It is preferable for the reconstruction of the intermediate images not to switch over harshly between the readings of the contributing measurement scans in order to reduce inconsistency artifacts—rather, there is a soft cross-fading in a transitional area between the two scanning sections of the two measurement scans that augment one another to form a complete measurement scan. Thus, when the method is carried out as preferred with the aid of a computer tomograph, in a specific angular range of the rotary frame, the measured data of the two contributing measurement scans are superposed with increased weighting from one measurement scan to the other. In the remaining angular or scanning ranges, only the measured data of one or the other measurement scan are used for the reconstruction.

The method of at least one embodiment permits the reconstruction and display of each main image directly at the end of the associated measurement scan such that no sort of delay times occasioned by the generation of intermediate images occur any longer. This is achieved by already calculating the intermediate image before termination of the respectively current measurement scan. Here, the current location information from the measured data features as well as possible in each intermediate image so that with reference to quality and use these images equal the images reconstructed from a complete measurement scan and, in particular, are far superior to the intermediate images of the prior art interpolated from adjacent main images.

Of course, in the case of all the possibilities of refinement for the method of at least one embodiment, the reconstruction of the main and intermediate images can already have been begun in each case as soon as the first measured data are present for the reconstruction so as to keep the delays occasioned by the reconstruction as short as possible.

The method of at least one embodiment can be carried out in principle with the aid of all the tomographic imaging facilities if the aim is to generate intermediate images when imaging with the aid of these facilities. However, the method of at least one embodiment offers particular advantages in the case of the imaging technique, advanced in the introduction to the description, with the aid of a computer tomograph, wherein the X-ray radiation of the examination object is switched off during each revolution of the rotary frame for a specific angular range in order to reduce the radiation burden.

Since it is not possible in each case to assume that two consecutive measurement scans begin at the same angular position of the rotary frame in such a mode of a computer tomograph, the angular range of the data from which the intermediate images are reconstructed can deviate within certain limits from the angular range of the data for the main images.

It is impermissible for measured data from measurement scans between which a longer time period with a possible variation in the lying position of the computer tomograph has passed to be processed to form an intermediate image. This control can be integrated into the method by monitoring this time interval and prescribing a limiting value for the time interval. The time interval between the starting times of two consecutive measurement scans with reference to the rotation time of the rotary frame can, for example, be evaluated as criterion for the limiting value.

BRIEF DESCRIPTION OF THE DRAWINGS

The present method is explained again in more detail below with the aid of example embodiments in conjunction with the drawings in which:

FIG. 2 shows a schematic of the temporal cycle of the measurement scans, and the illustration of the associated main and intermediate images in accordance with the prior art;

FIG. 3 shows a schematic of the temporal cycle of the measurement scans, and the illustration of the associated main and intermediate images in accordance with an example embodiment of the method;

DETAILED DESCRIPTION OF THE EXAMPLE EMBODIMENTS

Figure 1:
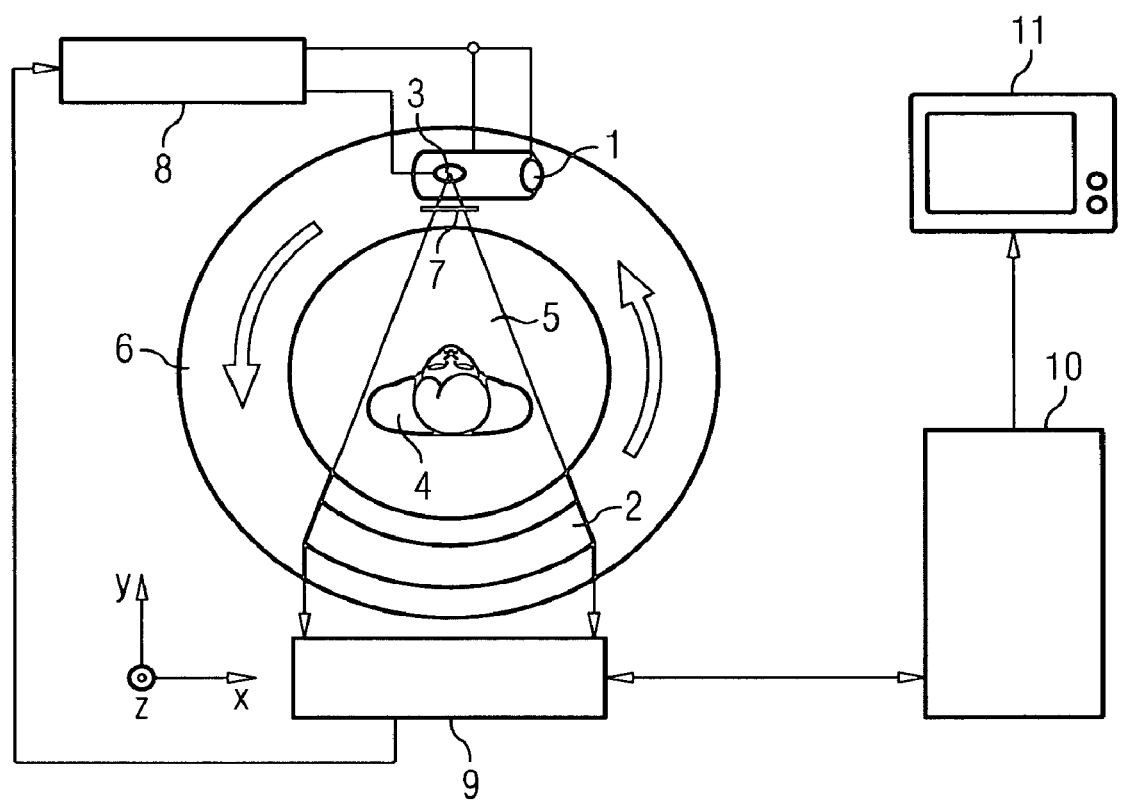
FIG. 1 shows a schematic of a computer tomograph for carrying out a method of an example embodiment.

FIG. 1 shows in a schematic a part of the design of an X-ray computer tomograph such as can be used to carry out a method of an example embodiment. The computer tomograph has an X-ray source in the form of an X-ray tube 1 that emits a fan-shaped X-ray beam 5 in the direction of a detector row with X-ray detector elements 2. Both the X-ray tube 1 and the detector elements 2 are arranged on a rotary frame 6, the so-called gantry, that continuously rotates about a patient 4 during a measurement.

The patient 4 lies on a patient couch (not illustrated in FIG. 1) that extends into the gantry 6. The gantry 6 rotates in an x-y plane of a Cartesian coordinate system x-y-z indicated in FIG. 1. The patient couch can be moved along the z-axis which corresponds to the thickness direction of the slices of the patient 4 that are respectively to be displayed.

The extent of the X-ray beam 5 in the z-direction, the direction perpendicular to the plane of the drawing in the present illustration, is prescribed, on the one hand, by the extent of the focus 3 on the rotating anode of the X-ray tube 1. On the other hand, it is prescribed by the diaphragm 7 arranged on the tube side and whose diaphragm aperture can be adjusted in the z-direction.

The X-ray tube 1 is supplied with a high voltage of, for example, 120 kV via a high voltage generator 8. A control 9 serves for driving the individual components of the computer tomograph, in particular of the high voltage generator 8, the gantry 6, the detector elements 2 and the patient couch in order to pick up the measured data. The measured data supplied by the detectors 2 are passed on to an image computer 10 in which the image reconstruction, the reconstruction of the main and intermediate images in the case of a method of an example embodiment, from the measured data is carried out. The image computer 10 displays these images in temporal sequence on a monitor 11.

In the case of invasive operations, the X-radiation is interrupted for a short time during each individual revolution of the rotary frame 6 in order to avoid the radiation burden on the examining physician. Instead of a continuous measurement scan lasting over a number of revolutions, this results in a series of individual measurement scans, as illustrated in FIG. 2 by example with the aid of three consecutive measurement scans 12(1)-12(3) for three revolutions of the rotary frame. Measurement pauses in which no measured data are acquired lie between the individual measurement scans 12(1)-12(3). The rotary frame 6 on which the angular range $\Delta\alpha_H$ of the measured data acquisition can be recognized for each measurement scan is illustrated schematically in the lower part of the figure. Each of the individual measurement scans 12(1)-12(3) begins at the angular position $\alpha$.

In the case of the known methods, intermediate images 14(1+2), 14(2+3) are interpolated in each case from the main images 13(1), 13(2) of two adjacent measurement scans 12(1), 12(2). As is to be recognized from FIG. 2, the second measurement scan 12(2) must be ended for the interpolation of the intermediate image 14(1+2) from the two main images 13(1) and 13(2), since not until then can the main image 13(2) be completely reconstructed. The first possible instant of the display of this intermediate image 14(1+2) therefore lies directly at the end of the second measurement scan 12(2). A rational display of image series therefore requires delaying the main image 13(2), which is of high quality, in relation to the end of the second measurement scan 12(2), as is illustrated in FIG. 2. The main images 13(1) and 13(2) are artificially delayed in this case by the time of half a rotation of the rotary frame 6.

This delay can be completely avoided when carrying out a method of an example embodiment, as may be seen from FIG. 3. In this example embodiment, the main images 13(1), 13(2) and 13(3) are respectively displayed at the end of the associated measurement scans 12(1), 12(2) and 12(3), and the intermediate images 14(1+2) and 14(2+3) are respectively displayed temporally in the middle of the respectively current measurement scan 12(2) or 12(3). This possibility results from the present fashion of calculating the intermediate images 14 which are reconstructed directly from the raw data and not interpolated from the image data of adjacent main images 13.

The measured data still missing in the case of the current measurement scan 12, at the instant when the intermediate image 14 is generated, are supplied by the preceding measurement scan. This fashion of generating images also leads to a substantially improved image quality by comparison with interpolation from two adjacent main images.

Figure 4:
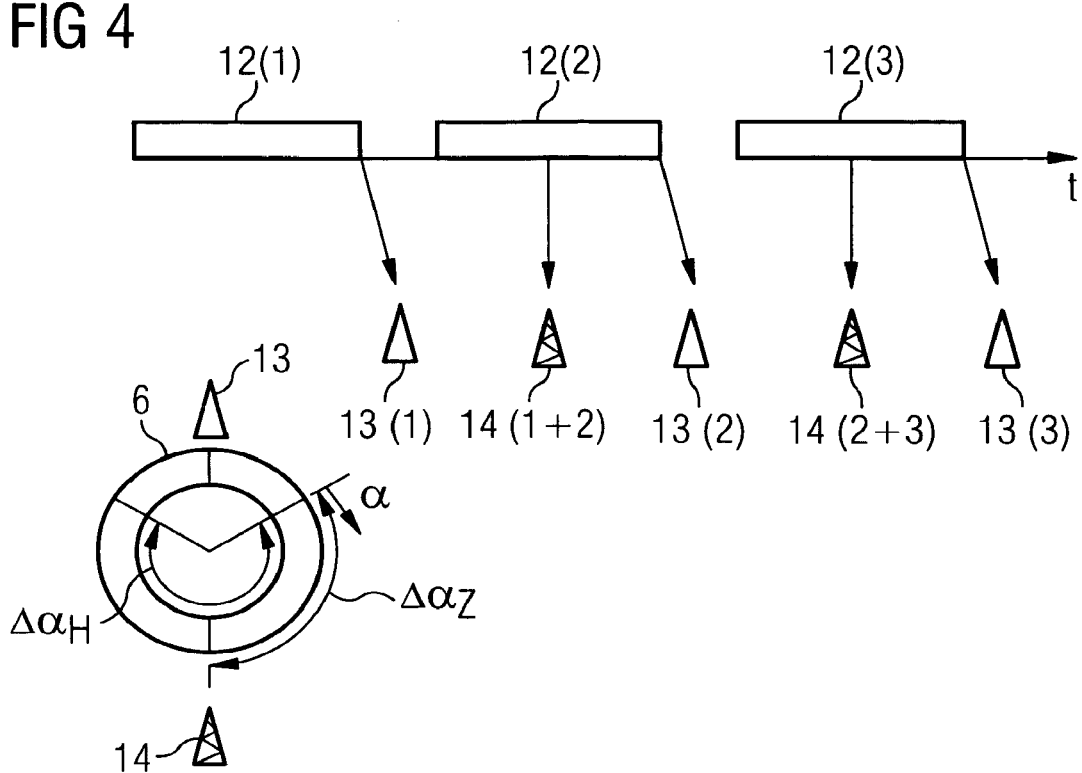
FIG. 4 shows a schematic of the temporal cycle of the measurement scans, and the illustration of the associated main and intermediate images in accordance with a second example embodiment of the method.
Figure 5:
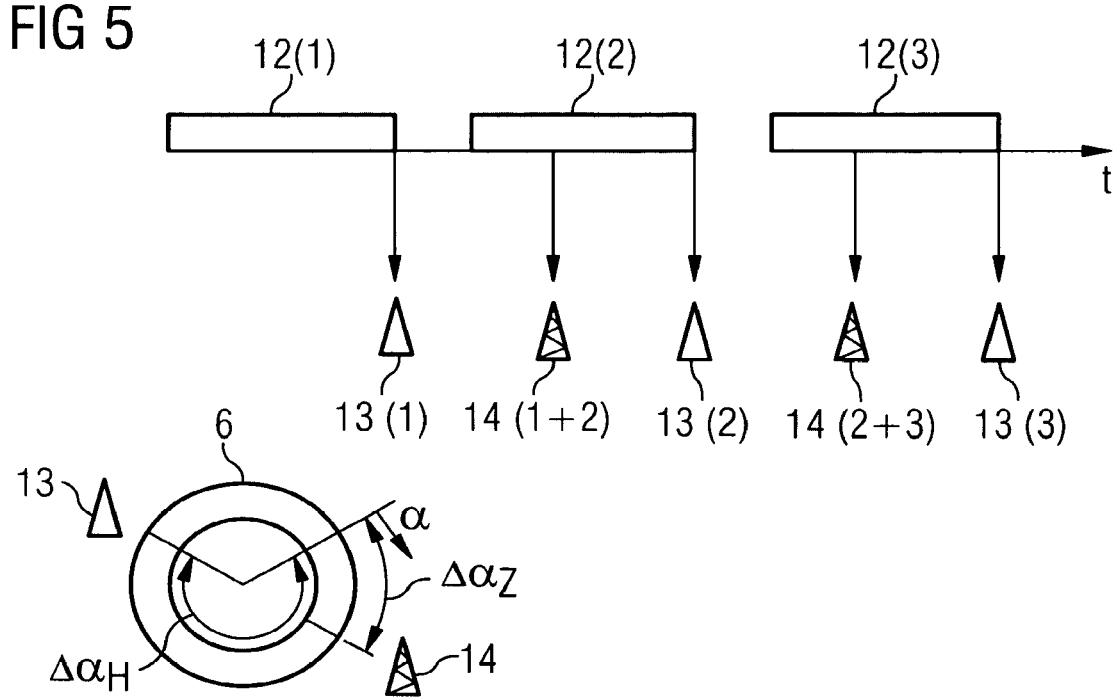
FIG. 5 shows a schematic of the temporal cycle of the measurement scans, and the illustration of the associated main and intermediate images in accordance with a third example embodiment of the method.

A temporally irregular series of images results in the present example embodiment from the fact that the main images 13 are displayed without being delayed by the generation of intermediate images, and that the intermediate images 14 are displayed in the middle of the respective measurement scan 12. If a uniform series of images is required, this can be achieved either by displaying the main images 13 with a slight delay, or by reconstructing and displaying the intermediate images 14 ahead of time. This is illustrated in FIGS. 4 and 5.

A uniform time interval between all the images of the series of images can be achieved by temporally delaying the main images 13(1), 13(2), 13(3) if the intermediate image 14(1+2) or 14(2+3) continues to be reconstructed and displayed in the middle of the respectively current measurement scan 12(2) and 12(3). Here, the main images must be artificially delayed by $(1-\Delta\alpha_H/360°)/2 \times$ rotation time. A delay by 133 ms results from an acquisition angle of $\Delta\alpha_H=240°$ and a rotation time of 800 ms (=time for a complete revolution of the rotary frame 6). If this delay is not desired, there is also the possibility of advancing the time of reconstruction and display of the intermediate images, as may be seen with the aid of FIG. 5.

Here, the main images 13(1), 13(2) and 13(3) are respectively reconstructed and displayed directly after the end of the associated measurement scan 12(1), 12(2) and 12(3) while the intermediate images 14(1+2) and 14(2+3) are reconstructed and displayed later by half the rotation time. Given an acquisition angle of $\Delta\alpha_H=240°$, the angular range $\Delta\alpha_Z$ of the current measurement scan that features in the intermediate image is only $\Delta\alpha_H-180°=60°$, but therefore still contains relatively little new information. However, for each application it is possible to find a compromise between a delay in displaying the main images 13 and advancing the intermediate images 14, and this compromise can lie between the circumstances of the preceding example embodiments.

Given an adequate computing speed, it is also possible to calculate, between two main images, a number of intermediate images that differ from one another in that each further intermediate image increasingly processes more measured data from the current measurement scan.

In the case of the preceding examples for reducing inconsistency artifacts when reconstructing the intermediate images 14, it is preferable not to switch over harshly between the readings of the contributing measurement scans but to cross-fade softly in a specific transitional angular range. This can be performed, for example, with the aid of a $\cos^2$ function in an angular range of approximately 30° in which the raw data of the two contributing measurement scans feature in the reconstruction of the intermediate image with the weighting prescribed by the $\cos^2$ function.

The above described embodiments of the method may further be embodied in a physical device, as would be understood by one of ordinary skill in the art, including via use of the disclosed and/or illustrated examples.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for imaging, comprising:
   acquiring, via a number of consecutive measurement scans, an object volume of an examination object;
   obtaining a series of main images by reconstructing each respective main image from measured data of each respective measurement scan and displaying the main images in temporal sequence; and
   calculating intermediate images to raise an image repetition rate and displaying the intermediate images between the main images,
       wherein the intermediate images are reconstructed at a prescribed instant within respective current measurement scans directly from a combination of measured data, acquired up to the prescribed instant, of the respective current measurement scan and measured data of a respectively preceding measurement scan that are still lacking for a complete reconstruction;
       wherein the combination of the already acquired measured data of the current measurement scan and the measured data of the preceding measurement scan is performed by augmenting the measured data of the current measurement scan with the measured data of the preceding measurement scan,
       wherein the current measurement scan corresponds to a first scanning section of a complete measurement scan and the preceding measurement scan corresponds to a remainder of a scanning section of the complete measurement scan and
       wherein the already acquired measured data of the current measurement scan and the measured data of the preceding measurement scan are combined in a transitional area of the first scanning section and the remaining scanning section using a cross-fading function such that in the transitional area a weighted mixing between the measured data of the current measurement scan and the measured data of the preceding measurement scan features in the reconstruction.

2. The method as claimed in claim 1, wherein the measurement scans are carried out with a computer tomograph, a main image being reconstructed and displayed for each complete revolution of a rotary frame of the computer tomograph.

3. The method as claimed in claim 2, wherein no measured data are acquired in a prescribed angular range of each revolution of the rotary frame such that each measurement scan extends over an angular range of only $\Delta\alpha_H < 360°$.

4. The method as claimed in claim 1, wherein the main images are reconstructed and displayed in each case directly after termination of the associated measurement scan, and wherein the intermediate images are reconstructed and displayed at least at an approximately equal temporal distance between two consecutive main images in each case.

5. The method as claimed in claim 1, wherein the main images are reconstructed and displayed in each case directly after termination of the associated measurement scan, and wherein the intermediate images are reconstructed and displayed at least at an approximately equal temporal distance to the start and end of the respective current measurement scan.

6. The method as claimed in claim 1, wherein the intermediate images are reconstructed and displayed at least at an approximately equal temporal distance at the start and end of the respective current measurement scan, and wherein the main images are reconstructed and displayed at least at an approximately equal temporal distance between two consecutive intermediate images in each case.

7. The method as claimed in claim 1, wherein the imaging method is for imaging with the aid of a tomographic imaging facility.

8. The method as claimed in claim 1, wherein the imaging method is for imaging with the aid of a computer tomograph.

* * * * *